(12) United States Patent
Bubel (10) Patent No.: US 7,197,968 B2
(45) Date of Patent: Apr. 3, 2007

(54) SCREWDRIVER WITH ADJUSTABLE DEVICE TO LIMIT TRANSMITTED TORQUE

(75) Inventor: Rainer Bubel, Neustadt/Hessen (DE)

(73) Assignee: Felo-Werkzeugfabrik Holland-Letz GmbH (DE)

(*) Notice: Subject to any disclaimer, the term of this patent is extended or adjusted under 35 U.S.C. 154(b) by 0 days.

(21) Appl. No.: 11/126,087

(22) Filed: May 10, 2005

(65) Prior Publication Data

US 2006/0016300 A1  Jan. 26, 2006

Related U.S. Application Data

(63) Continuation of application No. PCT/IB04/02917, filed on Sep. 6, 2004.

(30) Foreign Application Priority Data

Sep. 10, 2003  (DE) .................. 103 41 697

(51) Int. Cl.
*B24B 23/157* (2006.01)
*F16D 7/02* (2006.01)

(52) U.S. Cl. ............... 81/475; 81/473; 81/476; 192/56.62

(58) Field of Classification Search .......... 81/473–476, 81/58.3, 58.4; 192/56.62, 56.1, 110 R, 150; 464/38, 41
See application file for complete search history.

(56) References Cited

U.S. PATENT DOCUMENTS

| 2,335,574 | A | | 11/1943 | Thompson et al. | |
|---|---|---|---|---|---|
| 2,396,040 | A | * | 3/1946 | Darling | 74/126 |
| 2,410,971 | A | * | 11/1946 | Hartley | 81/475 |
| 2,771,804 | A | * | 11/1956 | Better et al. | 81/474 |
| 2,797,564 | A | * | 7/1957 | Bonneau et al. | 464/38 |

(Continued)

FOREIGN PATENT DOCUMENTS

DE   884 780   7/1953

(Continued)

OTHER PUBLICATIONS

Joseph R. Cruse, Jr., Declaration of Prior Invention in the United States in Protest to Cited Publication, Feb. 27, 2006, 2 pages and 2 Sheets Drawings.

*Primary Examiner*—Lee D. Wilson
*Assistant Examiner*—Anthony Ojini
(74) *Attorney, Agent, or Firm*—Leydig, Voit & Mayer, Ltd.

(57) ABSTRACT

A screwing tool with a device to adjust transmitted torque comprises a handle to introduce a torque to the device, which is borne in the hollow of the handle and a drive shaft as an output element of the torque. On the drive shaft inside the handle, two separate couplings are assembled, having between them a compression spring exerting a spring force against the two couplings. Each coupling comprises a first and a second socket engaging each other by gearings at their opposing faces. The maximum torque at which the torque transmission will be interrupted can be adjusted by an adjustment element wherein the distance between the couplings can be changed, thereby resulting in a change of the tension of the spring exerting a load on the couplings. The teeth of the gearings slide and the sockets rotate relatively to each other and interrupt the torque-transmission if a preadjusted torque is exceeded.

25 Claims, 6 Drawing Sheets

U.S. PATENT DOCUMENTS

| | | | |
|---|---|---|---|
| 2,884,103 A | * | 4/1959 | Connell .................. 192/56.53 |
| 4,063,474 A | | 12/1977 | Klopping |
| 5,746,298 A | * | 5/1998 | Krivec et al. .............. 192/48.3 |
| 6,487,943 B1 | | 12/2002 | Jansson et al. |

FOREIGN PATENT DOCUMENTS

| | | |
|---|---|---|
| DE | 24 47 352 A1 | 12/1975 |
| DE | 26 47 996 A1 | 5/1977 |
| DE | 101 43 181 A1 | 5/2002 |
| EP | 1 092 510 A2 | 4/2001 |

* cited by examiner

SCREWDRIVER WITH ADJUSTABLE DEVICE TO LIMIT TRANSMITTED TORQUE

CROSS-REFERENCE TO RELATED PATENT APPLICATIONS

This patent application is a continuation of PCT/IB2004/002917 filed Sep. 6, 2004, entitled "Screwdriver With Adjustable Device To Limit Transmitted Torque," which designates the United States of America, and which is incorporated in its entirety herein by this reference.

FIELD OF THE INVENTION

The Invention concerns a screwing tool/screwdriver with a device to select a pre-selected maximum torque at which the transmission of torque from the handle to a screwdriver shank will be interrupted.

BACKGROUND OF THE INVENTION

Screwing tools with a device to limit transmitted torque are known in different systems, in application with hand screwdrivers and power tools. Of special interest under an aspect of the invention are such systems in which the torque is transmitted from the hand of the user through the handle of the tool to the shank of a screwdriver blade. Systems which have to be considered in relation to the system according to the invention are described in their construction and function below.

A screwdriver according to U.S. Pat. No. 5,746,298 with an adjustable torque limiting device is complicated in the construction of the torque transmitting coupling, which is made of metal. In the handle a rotatable shank is borne of which one end section is hexagon shaped in its cross-section. This end section is encompassed by six finger-shaped longitudinal end sections of a metal-sleeve which can turn relative to the shaft. Each of the finger-shaped end sections contacts one of the six flats of the six flats of the hexagon shaft-section and applies a spring force onto it. The finger-shaped end sections are encompassed by a collar-shaped element which is adjustable in a longitudinal direction and which applies a radial force onto the finger-shaped end sections, pressing them onto the flats of the hexagonal shaft section.

The closer the collar-shaped element is disposed to the end of the finger-shaped end section, the stronger the radial spring force applied onto the hexagonal shaft section and the higher the torque transmitted from the handle to the shank before the shank rotates relative to the sleeve with the finger-shaped end section via the handle, thereby interrupting the torque transmission. The production of this torque limiting device is expensive in its production. To adjust the desired torque-limit the handle has to be disassembled partly. This system therefore is not practical for use when different torque-values have to be adjusted.

DE OS 26 47 996 discloses a system which essentially consists of axial ball and roller bearings which are under axial load by a compression-spring. The balls and rollers are seated between discs and are disposed in cavities. One disc is connected with the torque-input element, and the other disc with the torque-output element of the device. If the torque exceeds a particular adjusted value, the force in circumferential direction will be higher than the axial force exerted by the spring holding the balls and rollers in their seats such that the balls and rollers come out of their seats and the discs rotate relative to each other, thereby interrupting the transmission of the torque.

DE OS 2427 352 describes a system in which the torque transmitting device consists of a first shank with a disc-shaped end section as a coupling element. Its front face has a wave-shaped profile in the circumferential direction. A second shank also has a disc-shaped end section as a coupling element with the same profile engaging with the end section of the first shank. By a compression of a pack of plate-ring-springs, an axial force is exerted on the first shank. If the torque is higher than the friction force between the two engaged coupling elements, they rotate relative to each other and the torque transmission is interrupted.

From DE OS 101 43 181 A1, a screwdriver with a device to limit a transmitted torque is known. The coupling between the handle and the screwdriver-shank consists of a tube-like metal part into which longitudinal short slots are cut. Small balls are sitting between disk-like coupling elements into which cavities are formed. The disk-like elements are under axial load via a compression spring. With a part of their bodies, the balls extend into the slots of the shaft tube. If the torque exceeds the adjusted value given by the pressure of the spring, the balls come out of their seats and are pressed into the slots in the shaft tube and the torque transmission is interrupted. The construction basically corresponds to the construction as described by DE OS 26 47 996. The device according to DE OS 101 43 181 A1 is expensive in its production because it consists of metal parts of high precision.

In a screwdriver with a torque-limiting device as described in EP 1 092 510 A2 a shaft is borne in a handle, said shaft having a spherical end surface to transmit an axial force onto the inner end surface of the hollow in the handle. The end section of the shaft is enlarged like a mushroom. The enlarged end section at its side opposite to its end surface is provided with a gear profile in the circumferential direction. This gear profile engages into a gear profile of corresponding shape which is formed into the rear end surface of a socket which is assembled axially moveable and rotateable onto the shaft. This socket is profiled at its circumferential surface with longitudinal flutes into which engage gear-like ribs standing radially from the surface of the hollow in the handle. Through these ribs, a torque is transmitted from the handle to the socket. A compression spring is assembled in the front section of the hollow and exerts an axial force onto the socket. The flanks of the teeth of the gear by which the socket and the enlarged end section of the shaft engage are inclined in one circumferential direction and are standing perpendicular to the longitudinal axis of the system in the other longitudinal direction. If a torque load is applied which is higher than the torque determined by adjusting a particular spring force in the direction of the inclined flanks, the teeth of the socket will slide at the flanks of the gear profile in the mushroom-shaped end of the shaft, lift out of the gear profile and rotate relative to each other. By this, the torque transmission from the handle to the shaft will be interrupted.

The disadvantage of this system is that the axial force of the spring is directed through the end surface of the shaft to the end surface of the hollow in the handle. This axial force is super-imposed by the axial force which is directed to the handle from the hand of a user. As a result, there will be relatively high friction between the end surface of the shaft and the end surface of the hollow. The torque value at which the transmission of torque will be interrupted is influenced not only by the axial force of the spring but also by the axial force of the hand respectively generating the friction between the end surface of the shaft and the end surface of the hollow in the handle. The desired torque limit will therefore not be kept within desired tolerances. Of advantage is that the essential parts of the device are produced of plastic material by injection molding. Of disadvantage is, however, that only a relatively low torque can be transmitted. At higher torque, plastic deformation of important parts occur, thereby reducing the functional precision of the system such that it may not be acceptable any more.

Some torque limiting devices as shortly described before are relatively expensive to produce because they are complicated in their construction and consist of metal parts formed by cutting, turning, milling, drilling etc. The adjustment of a particular torque can not be done easily or the functional precision is not satisfactory.

Nowadays, the demand for screwdrivers with a device allowing for easy adjustment of a limit for the transmitted torque has increased. Applications for such a tool include the fixing of tungsten-carbide cutting plates at machine tools and the assembling of electronic components or plastic parts. Corresponding with the increasing demand of this kind of tools is the demand for lower prices.

The object is to develop a tool of this kind which can be produced at relatively low cost, which can be used at torque loads covering the most applications for which such a tool can be used, which can be adjusted or set easily, which functions with high precision over a long time of use. This is solved by the subject of the invention.

SUMMARY OF THE INVENTION

The present invention provides a screwdriver having a handle for input of the torque, a screwdriver shank for output of the torque, the torque being transmitted from the handle to the shank through a torque-limiting device.

Said torque-limiting device comprises two couplings assembled on a tube-like drive shaft provided with gear teeth on its surface extending over its length. Between said couplings a compression-spring is arranged that exerts an axial force onto the couplings. Each coupling comprises two cylindrical sockets/bushes engaging each other by gear teeth at opposing sides. The first-socket/bush is connected with the handle by teeth on its surface. In its boring, the drive shaft can rotate, the ridge of the gear teeth of the drive shaft contacting the surface of the boring. The second socket/bush is connected with the drive shaft by a radial gearing in its boring with play so that an axial movement is possible.

By the force exerted by the compression spring, the teeth of the first and second sockets engage each other until the torque transmitted from the handle through the first socket is higher than the friction between the teethed front faces of the first and second socket. The teeth slide relative to each other, forcing the second socket to move axially against the spring force. By this movement, the transmission of the torque from the handle to the drive shaft will be interrupted. The profile of the teeth at the front side of the first and second sockets is constructed such that the flanks of the teeth are inclined at an angle α in the rotational direction of fastening the screws. The edges of the teeth are slightly rounded. The ridge of the teeth is flattened or also rounded. The flanks of the teeth in the rotational direction of unscrewing/loosening the screws stand are disposed under an angle of 0° relative to a radial plane that includes the longitudinal axis of the device. In this direction, no defined torque has to be adjusted or kept. Further, at flank-angle of 0°, it will be avoided that the shaft—and the screw—will be turned in the unscrewing direction when the teeth of the two sockets/bushes come into engaging position again after they have rotated relative to each other.

To adjust/set the desired torque limit, the rear coupling can be moved axially through an adjustment element, which is in contact at its front side with the rear side of the second socket and which can be turned from outside the rear end of the cap of the handle by means of a screwdriver or key. The front side of the adjustment element is constructed as flange with a generally helically-inclined surface. The rear front side of the second socket has the same shape such that the two inclined ring surfaces form a contact surface. By turning the adjustment element through the helical contact surfaces, the distance of the rear coupling from the front coupling can be changed, thereby changing the pre-tension of the spring between the two couplings. As a result, the value of the friction between the teeth of the first and second sockets will be changed. Between the flange of the adjustment element and the inner surface of the cap, an adjustment disc is arranged which has gear teeth at its front side. The disc also has teeth on its circumferential surface and by these teeth is rotatively coupled with the handle. The rear side of the flange of the adjustment element has gear teeth, as the adjustment disc does. Both teethed surfaces are pressed against each other by the force of the spring. By this pressure, the rest position of the adjustment element in the circumferential direction is kept as adjusted when the adjustment element is turned.

The adjustment element is provided with a pin at its rear side, the pin being borne in a boring of the cap of the handle and reaching to the outer surface of the cap. On the end surface of the pin there are scale-marks corresponding with a scale marked in the surface of the cap. The position of the scale-mark in the end surface of the pin to the scale in the surface of the cap indicates the value of the adjusted torque.

The drive shaft is provided with a hollow in the longitudinal direction with a hexagonal cross-section profile to receive exchangeable screwdriver–or nut-setter–blades with a hexagonal shank. In a preferred embodiment, the screwdriver shank extends to near the end of the drive shaft. In another embodiment, the drive shaft is provided with a chuck to receive exchangeable tool inserts.

By turning the drive shaft, the screwdriver blade is also turned. The rear end of the teeth shaft is supported axially in a boring in the adjustment element. As a result of this construction, the force axially exerted from the hand of the user onto the handle and the cap when using this tool is transmitted through the adjustment-disc and the adjustment element onto the drive shaft. The compression spring is not loaded by any hand force; therefore, the force of the spring is not influenced and has an effect only on the two couplings, however, and not on the axial bearing of the teeth shaft.

BRIEF DESCRIPTION OF THE DRAWINGS

The object of the present invention is more precisely examplaryly described together with the drawings wherein.

DETAILED DESCRIPTION OF THE PREFERRED EMBODIMENTS

Figure 1:
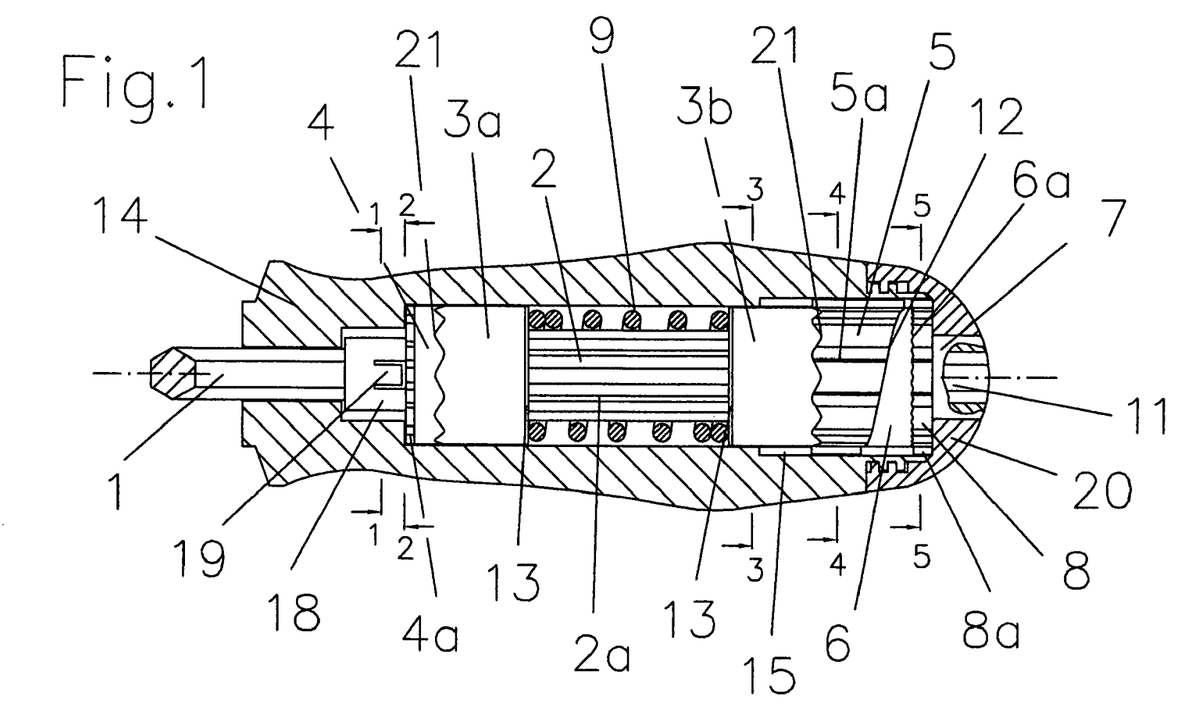
FIG. 1 is a fragmentary longitudinal sectional view through a screwing tool with a device to limit the transmitted torque.
Figure 2:
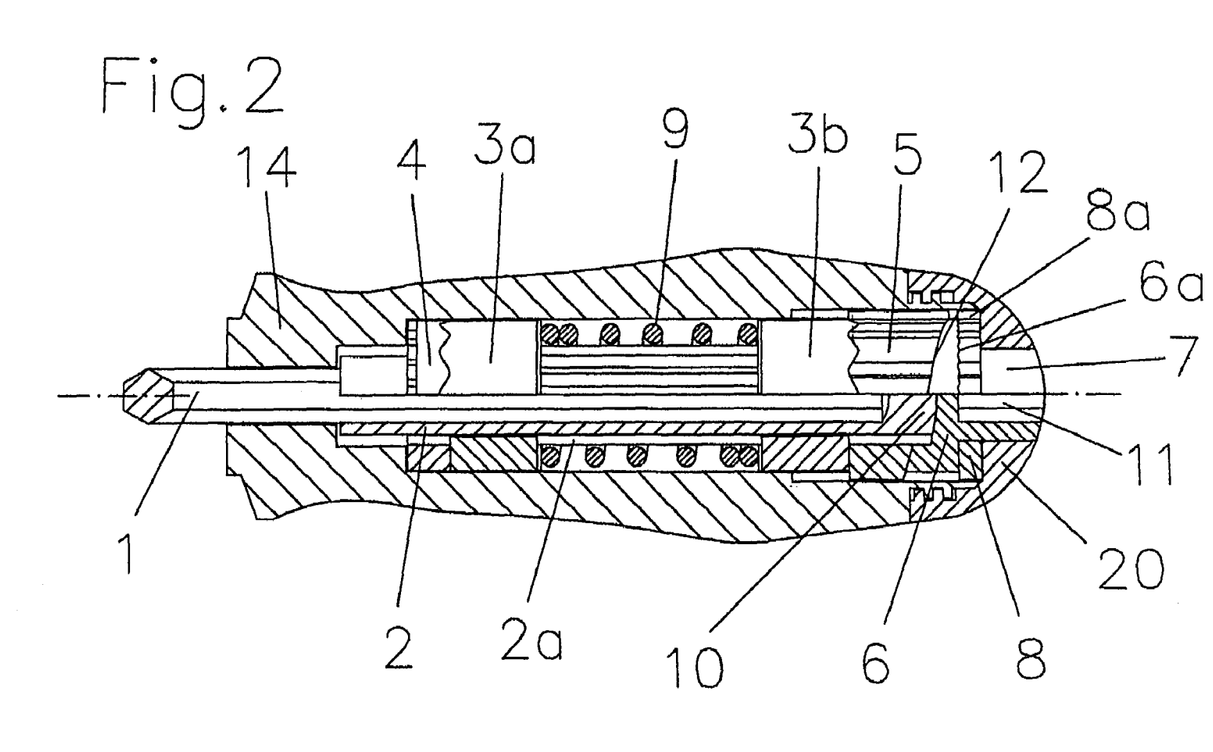
FIG. 2 is a second fragmentary longitudinal view, with the lower half in section reaching as far as to the shank end inserted into the drive shaft.

As FIG. 1 and FIG. 2 show, the screwing-tool according to the invention comprises a shank (1) with a non-circular cross-section profile, for example a hexagonal profile, seated in the drive shaft (2) and extending up to near the end of the teeth shaft. Said shank (1) may be part of a screwdriver blade or of a holding device for screwdriver bits or for sockets. The drive shaft (2) is profiled at its circumference with a gear (2a) over almost the full length, the teeth having preferably a rectangular profile. The first sockets (3a, 3b) are assembled on the drive shaft (2). With their cylindrical surface, the first sockets (3a, 3b) serve also as radial bearing elements of the whole torque-limiting mechanism by contacting rotateably the wall of the hollow in the handle (14), said hollow being shut by a cap (20). With an inner radial gear (3d) in their boring (FIG. 5), the first sockets engage in the gearing (21) of the drive shaft (2). At one front-side, the first sockets (3a, 3b) have a gearing (21) with a wave-like tooth-profile wherein the teeth are rounded at the tips. The gearings (21) mesh in corresponding gearing of the second sockets (4, 5). At the other front-side, the second socket (4) has a gearing (4a) with a rectangular profile which engages in a gearing with the same profile in the bottom of the hollow in the handle (14). A compression spring (9) is assembled with pre-tension between the two couplings (3a, 3b), resting on two washers (13). The second socket (5) is shaped with helically-inclined end surface (12) at the side opposite to the gearing (21). This inclined surface (12) is in contact with a collar/flange of the same shape formed at the adjustment element (6). At its circumference-surface, this second socket has a gearing (5a) which meshes with a corresponding gearing (15) formed in the wall of the hollow of the handle (14). The adjustment element (6) is provided with a fine gearing (6a) at the side opposite to the collar/flange (12).

A pin (7) is formed at the adjustment element. Said pin is borne in borings in an adjustment disk (8) and the cap (20) of the handle. A recess (11) is molded into the end of the pin (7) to allow for use of a hexagonal key—in the illustrated example—for turning the adjustment element (6). Between the adjustment element (6) and the cap (20), the adjustment disc (8) is arranged. The adjustment-disc (8) is provided with a rectangular gearing (8a) at its circumferential surface that is rotatively coupled to a corresponding gearing in the hollow of the handle (14). The fine gearing (6a) of the adjustment element (6) engages with a corresponding gearing formed into the adjacent side of the adjustment disk (8).

If the adjustment element (6) is turned, the collar/flange (12) with spiral pitch contacts the second socket (5). This socket (5) together with the first socket (3b) is moved axially, thereby changing the pre-tens ion of the compression-spring (9). If a torque is applied on the handle (14), it will be transmitted by the gearings (4a, 15) into the second sockets (4, 5) and further by the gearings (21) to the first sockets (3a, 3b) from said first sockets to the drive shaft (2) and further to the shank (1).

The amount of pre-tension of the compression spring determines up to which torque the gearing (21) of the first sockets (3a, 3b) and the second sockets (4, 5) will remain engaged until by rotation of the first sockets and the second sockets relative to each other the transmission of the torque to the shank (1) will be interrupted.

A clamping device (18) at the front end of the drive shaft (2) holds the shank (1) inserted into the drive shaft (2) by spring force exerted by an elastic tongue-like or saddle-like element (19) formed into the drive shaft. In another embodiment, the clamping device comprises a band-ring-spring encompassing the front end of the drive shaft (2). In a radial boring in the front end of the drive shaft, a small steel ball is borne which at one side protrudes into the hollow (2b) of the drive shaft and at the other side protrudes out of the outer surface of the drive shaft. A radial force is exerted by the band-ring-spring on the steel ball. If the shank is inserted into the hollow, the steel ball is displaced radially outward and exerts a clamping force onto the shank.

FIG. 2 is a similar longitudinal section as FIG. 1; however, the drive shaft (2) in the lower half of the section is cut in section up until its end. It may be seen that the inserted shank (1) extends to near the end of the drive shaft.

Figure 3:
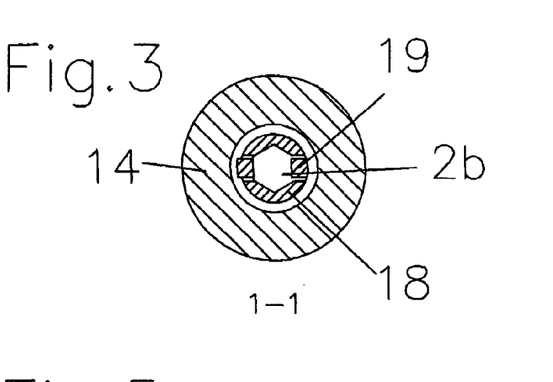
FIG. 3 is a cross-sectional view along line 1—1 in FIG. 1 through a clamping device of the drive shaft, without the shank inserted therein.

FIG. 3 shows a cross-section along line 1—1 in FIG. 1 only through a clamping device (18, 19) of the embodiment with the shank inserted exchangeably in the drive shaft. The shank is borne unrotatably in a pre-molded hollow extending longitudinally in the drive shaft and held by a clamping device (18) at the front end of the drive shaft (2). The clamping device (18) is molded as a cylindrical part of the drive shaft with a tongue-like or saddle-like elastic element (19) reaching with its lower end into the hollow (2b) of the drive shaft and being flexed radially outward when the shank is inserted into the hollow. The spring force of the flexed elastic element holds the shank in its longitudinal position. In another embodiment, the clamping device comprises a band-ring-spring encircling the front end of the drivershaft (2). In a radial boring in the front end of the drive shaft, a small steel ball is borne which at one side protrudes into the hollow (2b) of the driver-shaft, and at the other side protrudes out of the outer surface of the drive shaft. A radial force is exerted by the band-ring-spring on the steel ball. If the shank is inserted into the hollow, the steel ball is displaced radially outward and exerts a clamping force onto the shank.

Figure 4:
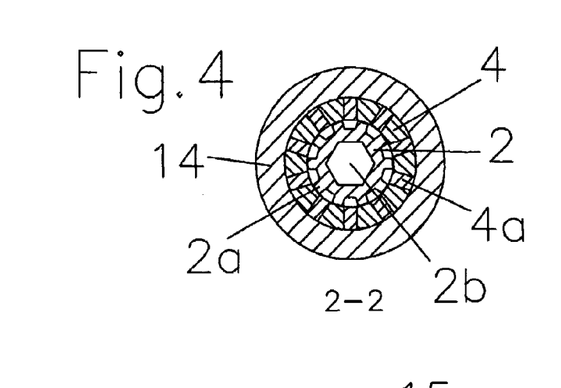
FIG. 4 is a cross-sectional view along line 2—2 of FIG. 1 without the shank inserted therein.

FIG. 4 shows a cross-section along line 2—2 in FIG. 1. As can be seen, the gearing (4a) of the second socket (4) engages with a corresponding gearing in the handle (14) and connects both parts such that they can not rotate relative to each other. The drive shaft (2) with its gearing (2a) is borne rotateably in the second socket (4). The hollow (2b) for receiving the hexagonal shank (1) also can be seen.

Figure 5:
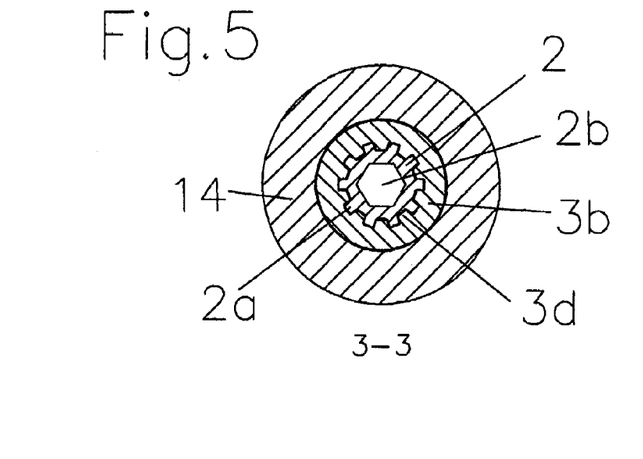
FIG. 5 is a cross-sectional view along line 3—3 in FIG. 1 without the shank inserted therein.

FIG. 5 shows a cross-section along line 3—3 in FIG. 1. It can be seen that the first socket (3b) is borne rotatably by its cylindrical circumferential surface in the hollow of handle (14). The first socket (3a) is linked by an inner gearing (3d) with the gearing (2a) of the drive shaft (2). By the same way, the other first socket (3a) is also linked with the drive shaft (2) and borne in the handle.

Figure 6:
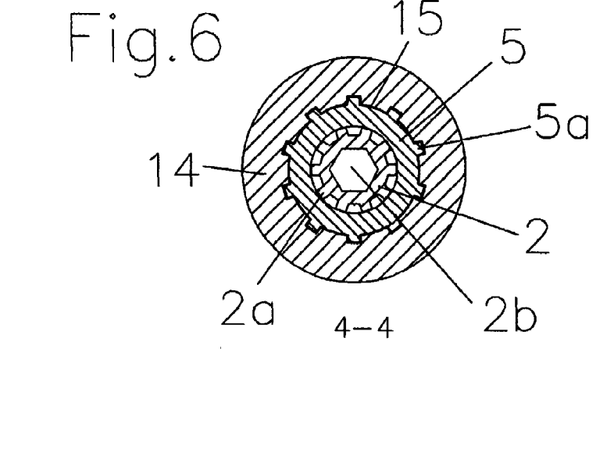
FIG. 6 is a cross-sectional view along line 4—4 in FIG. 1 without the shank inserted therein.

FIG. 6 shows a cross-section along line 4—4 in FIG. 1. The second socket (5) is linked by its gearing (5a) with the gearing (15) of the handle (14). The drive shaft (2) is borne rotateably in the second socket (5).

Figure 7:
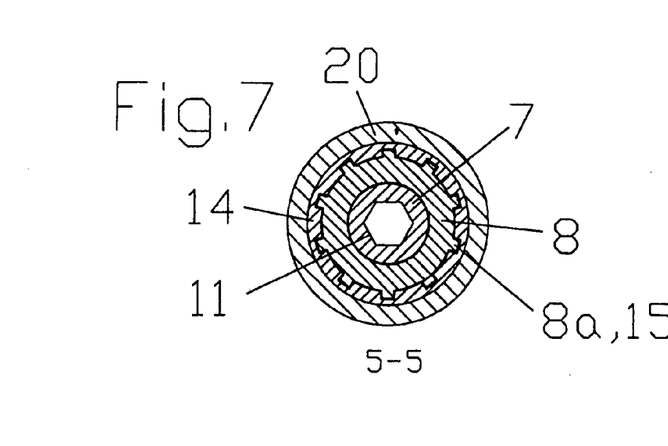
FIG. 7 is a cross-sectional view along line 5—5 in FIG. 1 without the shank inserted therein.

FIG. 7 shows a cross-section along line 5—5 in FIG. 1. The gearing (8a) of the adjustment disc (8) engages with the gearing (15), thereby firmly unturnably linking the adjustment disc (8) with the handle (14). The pin (7) of the adjustment element (6) having the recess (11) is borne rotateably in the adjustment disc (8).

Figure 8:
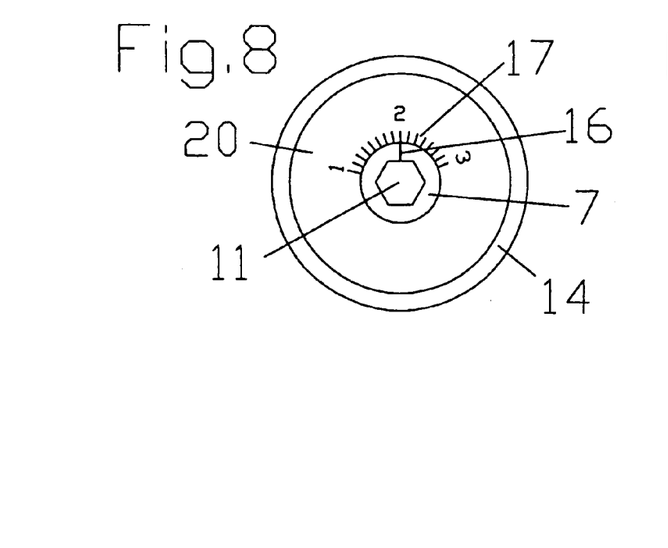
FIG. 8 is a plan view of the screwing tool of FIG. 1 from the rear side showing the cap of the handle.

Referring to FIG. 8, scale marks (16) on the pin (7) and the cap (20) are shown as a principle of the marking. For use, it may be suitable to fix at the cap a scale-disc marked with the torque-value figures which can be adjusted.

As explained before, the range of adjustable torque values depends from the spring-characteristic of the spring (9) inserted in the device, and this range can be measured by calibrating the torque-adjusting-system. The construction of the adjustment element (6) and the second socket (5) with spiralic pitched engaging/contacting surface (12) allows for the ability to achieve a very precise calibration. The pitch of the surfaces (12) at the second socket (5) and at the adjustment element (6) determines how much the transmittable torque will change for a particular angle of turn of the adjustment element (6). If the pitch is low, the second socket (5) and the first socket (3b) will be moved axially only by a small distance for a particular angle of turn of the adjustment element. Consequently, the length of the compression spring (9) will change only by this small distance, and, correspondingly the pre-tension of the spring and the transmittable torque will change only slightly.

Figure 9:
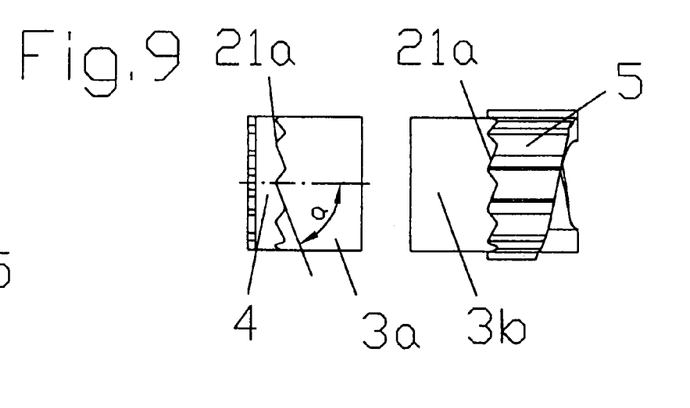
FIG. 9 is a side elevational view of the first and second sockets of the first coupling and first and second sockets of the second coupling.
Figure 10:
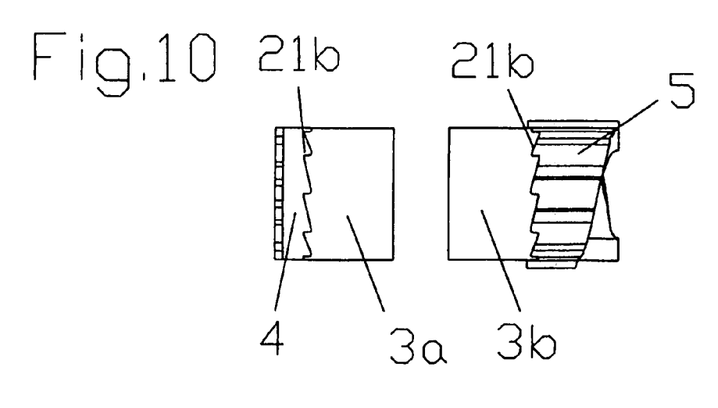
FIG. 10 is a side elevation view on the first and second sockets of the first coupling and first and second sockets of the second coupling with a variation of the teeth profile.

FIGS. 9 and 10 show the couplings with different shapes of the gear (21a, 21b). By the shape of the tooth, the torque at which the teeth start to slide at the flanks and disengage can be influenced. If the angle α of the flank is large relative to the longitudinal axis of the coupling, the teeth will start to slide at a lower torque than if α is small. If the angle α is 0°, as shown in FIG. 10 for a left-turn-direction, there will be no disengagement of the coupling at all. At this angle, it will be avoided also that a screw will be turned in the loosening/unscrewing direction again if the resistance of the screw to turn is low.

Figures 11, 12:
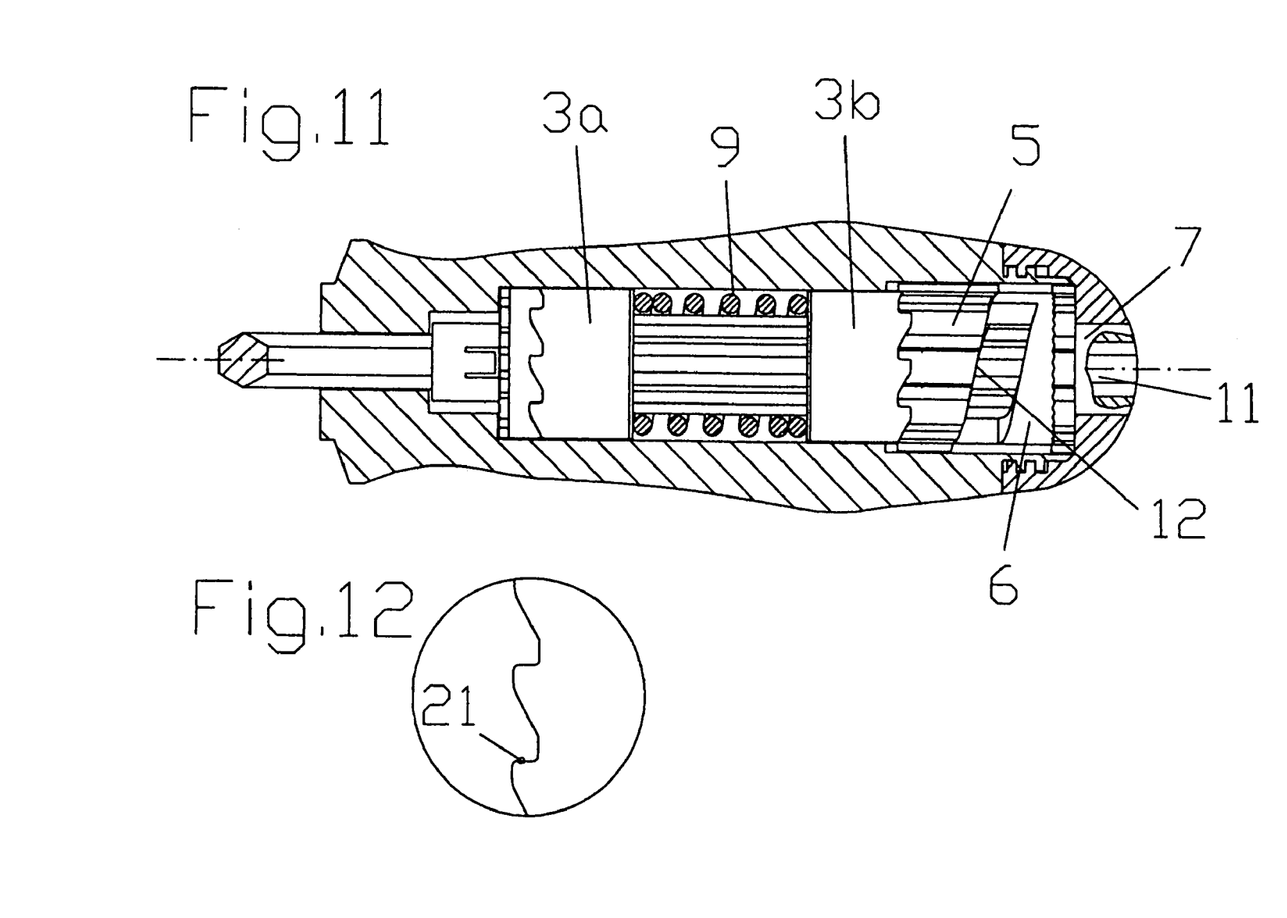
FIG. 11 is a longitudinal sectional view showing the rear coupling displaced in a direction toward the coupling in the front part of the handle and the spring more compressed.
FIG. 12 is an enlarged illustration of a section of the gear teeth of the engaging faces of the first and second socket of the couplings.

In FIG. 11, a longitudinal section through the screwing-tool, it is shown that the first and second sockets (3b, 5) of the second/rear coupling are displaced forward in a direction toward to the first coupling by turning the adjustment element (6). By this, the compression spring (9) has been more compressed, the wide gap between the low area of the spiral-pitched collar/flange of the adjustment element (6) and the spiral-pitched end surface (12) of the second socket (5) being clear. By turning the adjustment element (6) by means of a key inserted into the recess in the pin, a pre-determined torque can be set to be transmitted via the shank (1). By calibrating the torque-transmitting device, the values of adjustable torque can be found and marked on scales (6, 7) at the end of the handle. By selecting the compression spring (9) with a particular spring characteristic, the desired adjustable torque values can be determined.

It is also possible to cover different ranges of adjustable torque values by removing the cap (20) from the handle (14), exchanging the compression spring (9) with a spring having another spring characteristic, and re-assembling the device and cap. The adjustment element (6) serves also as a bearing for the end (10) of the drive shaft (2), especially as an axial bearing as shown in FIG. 2. Axial forces are transmitted from the adjustment element (6) through the adjustment disc (8) the cap (20) or transmitted in the other direction during use of the screwdriver from the hand of the user to the handle (14) and the cap (20) to the shank (1). In another embodiment, the shank (1) is firmly inserted into the drive shaft (2).

Figure 13:
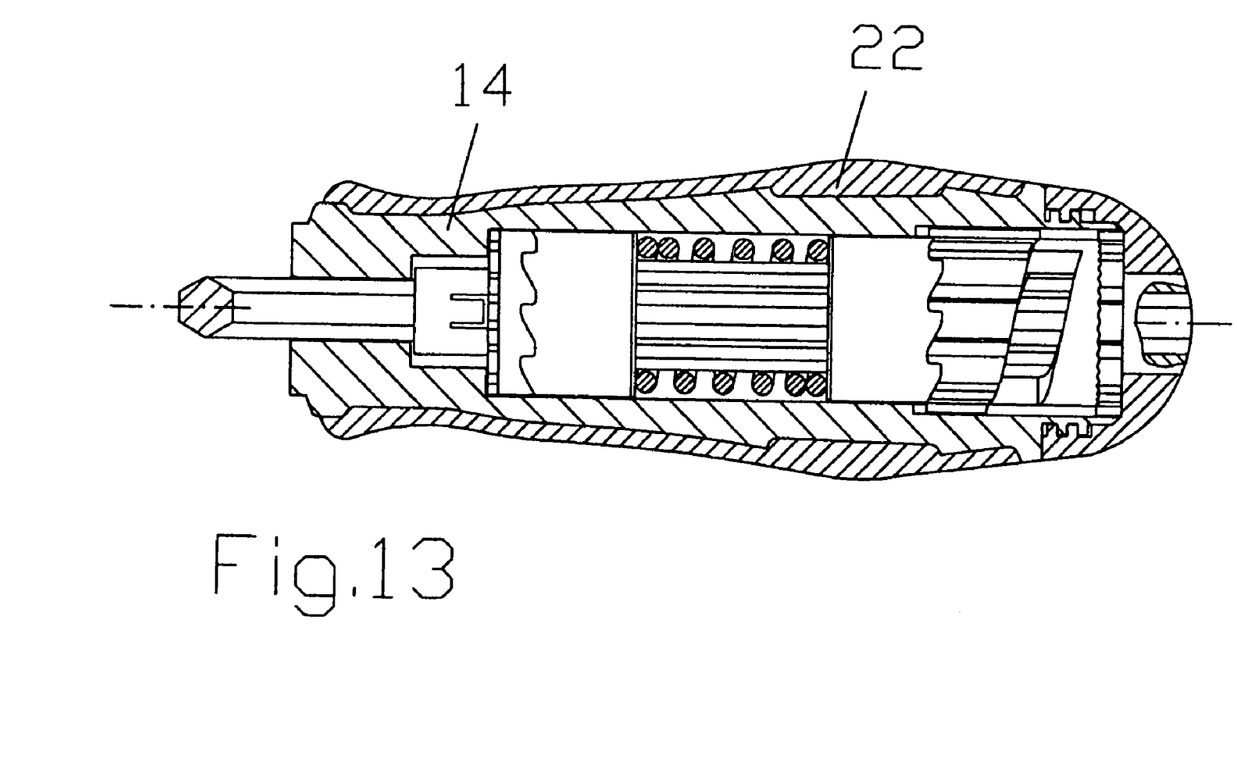
FIG. 13 is a fragmentary longitudinal sectional view through another embodiment of a screwing tool showing an embodiment of the handle with a coat of soft plastic material.

FIG. 12 shows in a larger scale the preferred wave-like shape of the teeth of the gearing (21) by which the first and second sockets of the two couplings engage each other. In FIG. 13, an embodiment of the handle (14) is illustrated which has a coat (22) of soft plastic material injection molded onto the core handle made of hard plastic material.

The construction of the device with two couplings and the other elements according to the present invention allows one to transmit higher torque than by known devices because the specific loads on the different torque-transmitting elements are much lower than by a device with one coupling only. This is achieved by introducing torque at two areas, namely through the gearing (4a) at the front side face of the second socket (4) and through the gearing (5a) at the circumferential surface of the second socket (5) via the inner gearing (15) of the handle (14), and transmitting torque to the drive shaft (2) also through two elements, namely the two first sockets (3a, 3b).

The lower specific loads at the torque-transmitting areas or elements allow one to produce all the parts of the device—with exception of the shaft (1),—the spring (9), and the washers (13) of plastic material by injection-molding. Polyamide (PA) and polyoxymethylene (POM) have been found to be suitable plastic materials, especially for those parts which are sliding against each other. Of special advantage is a composition of POM with Teflon or a sliding-improving additive to the basic material. Using this material, the friction between sliding surfaces is reduced remarkably which is of special importance at the gearing (21) of the first sockets (3a, 3b) engaged with the gearing of the second sockets (4, 5). By reduction of the friction the influence of the friction on the transmitted torque is reduced, which further improves the precision in function of the device.

Screwdrivers with a device to adjust a transmitted pre-selected torque are used also in orthopedic surgery. It is necessary to sterilize the instruments after use. In dry-air sterilizing apparatus, a temperature of 180° C. can be reached. No deformation of parts of the torque-adjusting device is allowed at this temperature.

In a special execution the screwing tool is made of plastic material which has a heat resistance and maintains shape stability up to 220° C. Particular parts, such as the teeth shaft (2), the first and second sockets (3a, 3b, 4, 5), the adjustment element (6), and the adjustment disc (8), or only some of these parts, may alternatively be made of metal, for example, as parts sintered of powder metal of a quality or metal pairing which have a good sliding characteristic. The parts may also be made of steel formed by turning, milling, or pressing. Also, the handle (14) and the cap (20) may be made of metal, for example, of aluminium as cast parts. Finally, the handle, the cap, and other parts of the device, especially those which have to withstand a static load during the use of the tool, may be made of stainless steel. The metal execution may be considered if with the same dimension as a plastic-material execution, higher torque has to be transmitted, or, for use in the orthopedic surgery, the tool has to withstand sterilization without any limit. As a metal handle will be designed considering the requirement of durability and not so much the requirements of ergonomics—to save weight—in a variation of the embodiment of the core handle, a non-circular outer cross-section contour can receive a sleeve preferably made of elastic plastic material. The outer contour of this plastic sleeve is shaped to meet the requirements of ergonomics. The sleeve may be withdrawn from the score handle and disposed after use of the tool. This embodiment is illustrated in FIG. 13.

The tool according to the present invention is of special advantage with respect to the adjustment of the torque. The spiralic-pitched collar/flange (12) of the adjustment element (6) in contact with the spiralic-pitched rear side face of the second socket (5) functioning together with the fine gearing (6a) of the adjustment disc (8) and of the adjustment element (6) allow one to adjust the pre-tension of the compression spring (9) in very fine steps resulting in a very precise adjustment of a pre-selected torque at which the torque-transmission is interrupted. If the tool is designed to be used as a calibrating tool for other torque-measuring tools, a low-pitch angle of the spiralic surfaces (12) can be chosen. Then, the torque values may be adjusted even more precisely.

By the arrangement of two couplings on the drive shaft (2), the pre-tension of the spring (9) is distributed equally on both couplings, the contacting surface is increased, and, consequently, the specific load on them reduced. The spring force does not exert an axial load on the drive shaft (2), thereby avoiding an influence by friction in the axial bearing of the drive shaft on the torque transmitted from the handle through the torque-adjusting and -limiting device to the shank (1).

Of advantage is also that all parts of the tool according to the present invention can easily be assembled. The tool can be produced at relatively low cost, function with high precision, and have long-lasting durability.

The invention claimed is:

1. A screwing tool with an adjustable device to limit transmitted torque, said device comprising a handle with an axially extending hollow in which a mechanism is arranged to interrupt the transmission of torque from the handle to a drive shaft if a pre-adjusted torque value is exceeded, said mechanism comprising a drive shaft on which two couplings are assembled, each coupling comprising a first and second socket which are engaging each other by a gearing at their opposing side faces, both first sockets are engaging with an inner gearing with a gearing on the circumferential surface of the drive shaft and are moveable in a longitudinal direction, both second sockets are rotatively coupled and in mesh with the handle by means of a gearing, and a compression spring arranged with pre-tension between the two couplings, said hollow in the handle being shut by a cap.

2. A screwing tool as defined in claim 1 wherein the first sockets are borne and radially supported with their cylindrical surface by the cylindrical hollow in the handle which encloses the sockets at least at a part of their longitudinal extension.

3. A screwing tool as defined in claim 1 wherein the second sockets have an axial boring in which the drive shaft is borne rotatably.

4. The screwing tool as defined in claim 1 wherein the second socket of the front coupling is rotatively coupled with the handle by a gearing at its front side.

5. The screwing tool as defined in claim 1 wherein the second socket of the rear coupling is borne moveably in a longitudinal, axial direction along the drive shaft, said second socket having a geared circumferential surface with which it is engaging in a gearing which is molded into this part of the hollow of the handle.

6. The screwing tool as defined in claim 1 wherein the rear end face of the second socked of the rear coupling is shaped as a spiralic pitched surface.

7. The screwing tool as defined in claim 1 wherein an adjustment element is arranged behind the second socket of the rear coupling, at this adjustment element the face opposite to the second socket of the rear coupling is also shaped as a spiralic pitched surface with which it contacts the spiralic surface of the second socket of the rear coupling, said adjustment element at the rear face has a fine gearing.

8. The screwing tool as defined in claim 1 wherein an adjustment disc is arranged between the adjustment element and the cap of the handle, said adjustment disc at its face opposite to the adjustment element also has a fine gearing engaging with the gearing of the adjustment element, both parts are pressed together by the force exerted by the compression spring.

9. The screwing tool as defined in claim 8 wherein the adjustment element has a pin with which it penetrates the adjustment disc and the cap of the handle and is borne in these parts, the pin has a recess at its end provided for to insert a key to turn the adjustment element.

10. The screwing tool as defined in claim 8 wherein the graduation of the gearing at the adjustment disc are so chosen that within a given range of torque values intermediate torque values can be adjusted in equal steps.

11. The screwing tool as defined in claim 10 wherein the surface of the pin and the surface of the cap around the pin are marked with scale marks and the position of the markings relative to each other indicate the pre-tension of the spring respectively the adjusted maximum torque which will be transmitted.

12. The screwing tool as defined in claim 1 wherein the gearing of the first and second sockets has a substantially triangular tooth-profile wherein the angle of the teeth-flanks relative to the axis of the sockets is larger in a screw fastening direction than in a screw loosening direction, the screw fastening direction being opposite to the screw loosening direction.

13. The screwing tool as defined in claim 1 wherein the angle a of the teeth-flanks relative to the axis of the sockets in a screw fastening direction is larger if the device is designed for a range of lower torques than if the device is designed for a range of higher torques.

14. The screwing tool as defined in claim 13 wherein the angle of the teeth-flanks relative to the axis of the sockets is 0° in a screw loosening direction.

15. The screwing tool as defined in claim 14 wherein the profile of the teeth is shaped wave-like and the teeth are rounded or flattened at their ridge.

16. The screwing tool as defined in claim 1 wherein the gearing at the drive shaft, in the boring of the first sockets, at the circumferential surface of the second socket of the rear coupling and in the hollow of the handle have a substantially rectangular tooth-profile.

17. The screwing tool as defined in claim 1 wherein the handle and the cap are connected by thread.

18. The screwing tool as defined in claim 1 wherein the drive shaft, the first and second sockets of the couplings, the adjustment element, the adjustment-disc, the compression spring, the handle and the cap are arranged such that there is no axial load exerted onto the drive shaft.

19. The screwing tool as defined in claim 1 wherein the axial force exerted by the compression spring is lead in one direction through the first and second socket, the adjustment element and the adjustment disc into the cap of the handle, in the other direction through the first and second socket into the front part of the handle.

20. The screwing tool as defined in claim 1 wherein the drive shaft, the first and second sockets, the adjustment element, the adjustment disc, the handle and the cap are made of plastic.

21. The screwing tool as defined in claim 20 wherein one of the parts with a surface sliding against a surface of another part is made of Polyamide (PA) and the other part is made of Polyoxymethylene (POM) where as at least at one part of the basic material is compounded with a sliding improving additive.

22. The screwing tool as defined in claim 20 wherein the plastic materials used have a heat-resistance up to 220° C.

23. The screwing tool as defined in claim 1 wherein at least one of the drive shaft, the first and second sockets, the adjustment element, the adjustment disc, the handle, and the cap is made of metal.

24. The screwing tool as defined in claim 1 wherein a core-handle made of metal has an outer cross-section contour which is non-circular and an ergonomically shaped handle-sleeve made of plastic material is removably assembled on the metal handle.

25. The screwing tool as defined in claim 1 wherein the shank of a screwdriver-blade or a holder for screwdriver-inserts (bits) is inserted exchangeably in the driver shaft and held its position by a clamping device connected with the driver shaft.

* * * * *

UNITED STATES PATENT AND TRADEMARK OFFICE
CERTIFICATE OF CORRECTION

PATENT NO. : 7,197,968 B2
APPLICATION NO. : 11/126087
DATED : April 3, 2007
INVENTOR(S) : Rainer Bubel It is certified that error appears in the above-identified patent and that said Letters Patent is hereby corrected as shown below:

ON THE TITLE PAGE: item 63

Column 1, line 9, "Sept. 6, 2004" should read --Sep. 8, 2004--.

Page 2: item 56 FOREIGN PATENT DOCUMENTS: "DE 24 47 352" should read --DE 24 27 352--.

IN THE SPECIFICATION:

Column 4, lines 32 and 34: "scale-marks" should read --scale marks--.

Column 4, line 58: "examplaryly" should read --exemplarily --.

Column 5, line 31: "screwing-tool" should read --screwing tool--.

Column 5, line 43: "rotateably:" should read --rotatably--.

Column 5, line 48: "tooth-profile" should read --tooth profile--.

Column 5, line 50: "front-side" should read --front side--.

Column 6, line 3: "adjustment-disc" should read --adjustment disc--.

Column 6, line 13: "compression-spring" should read --compression spring--.

Column 7, line 19: "rotateably" should read --rotatably--.

Column 7, line 22: "scale-disc" should read --scale disc--.

Column 7, line 27: "torque-adjusting-system" should read --torque adjusting system--.

Column 7, line 52: "screwing-tool" should read --screwing tool--.

Column 8, line 33: "(1), --the spring (9)" should read --(1), the spring (9)--.

Column 8, line 34: "(13) of plastic material by injection-molding" should read --(13)-- of plastic material by injection molding--.

UNITED STATES PATENT AND TRADEMARK OFFICE
CERTIFICATE OF CORRECTION

PATENT NO. : 7,197,968 B2
APPLICATION NO. : 11/126087
DATED : April 3, 2007
INVENTOR(S) : Rainer Bubel

It is certified that error appears in the above-identified patent and that said Letters Patent is hereby corrected as shown below:

IN THE CLAIMS:

Claim 18, Column 10, line 65: "adjustment-disc" should read --adjustment disc--.

Signed and Sealed this

Thirteenth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,197,968 B2
APPLICATION NO. : 11/126087
DATED : April 3, 2007
INVENTOR(S) : Rainer Bubel It is certified that error appears in the above-identified patent and that said Letters Patent is hereby corrected as shown below:

ON THE TITLE PAGE:

Column 1, line 9, "Sept. 6, 2004" should read --Sep. 8, 2004--.

Page 2: FOREIGN PATENT DOCUMENTS: "DE 24 47 352" should read --DE 24 27 352--.

IN THE SPECIFICATION:

Column 4, lines 32 and 34: "scale-marks" should read --scale marks--.

Column 4, line 58: "examplaryly" should read --exemplarily --.

Column 5, line 31: "screwing-tool" should read --screwing tool--.

Column 5, line 43: "rotateably" should read --rotatably--.

Column 5, line 48: "tooth-profile" should read --tooth profile--.

Column 5, line 50: "front-side" should read --front side--.

Column 6, line 3: "adjustment-disc" should read --adjustment disc--.

Column 6, line 13: "compression-spring" should read --compression spring--.

Column 7, line 19: "rotateably" should read --rotatably--.

Column 7, line 22: "scale-disc" should read --scale disc--.

Column 7, line 27: "torque-adjusting-system" should read --torque adjusting system--.

Column 7, line 52: "screwing-tool" should read --screwing tool--.

Column 8, line 33: "(1), --the spring (9)" should read --(1), the spring (9)--.

Column 8, line 34: "(13) of plastic material by injection-molding" should read --(13)--of plastic material by injection molding--.

UNITED STATES PATENT AND TRADEMARK OFFICE
CERTIFICATE OF CORRECTION

PATENT NO. : 7,197,968 B2
APPLICATION NO. : 11/126087
DATED : April 3, 2007
INVENTOR(S) : Rainer Bubel

It is certified that error appears in the above-identified patent and that said Letters Patent is hereby corrected as shown below:

IN THE CLAIMS:

Claim 18, Column 10, line 65: "adjustment-disc" should read --adjustment disc--.

Signed and Sealed this

Twenty-seventh Day of November, 2007

JON W. DUDAS
*Director of the United States Patent and Trademark Office*